United States Patent [19]

Layer

[11] 4,054,551
[45] Oct. 18, 1977

[54] BENZOFURANYLPHENOL STABILIZERS

[75] Inventor: Robert W. Layer, Cuyahoga Falls, Ohio

[73] Assignee: The B. F. Goodrich Company, Akron, Ohio

[21] Appl. No.: 573,819

[22] Filed: May 2, 1975

[51] Int. Cl.$^2$ .............................................. C08K 5/15
[52] U.S. Cl. ........................ 260/45.8 A; 260/346.22; 260/800
[58] Field of Search .......... 260/45.8 A, 800, 85.5 HC, 260/94.3, 346.2 R

[56] References Cited

U.S. PATENT DOCUMENTS

| | | | |
|---|---|---|---|
| 1,779,390 | 10/1930 | Clifford | 260/800 |
| 2,320,746 | 6/1943 | Paul | 260/800 |
| 2,362,479 | 11/1944 | Gibbs | 260/800 |
| 2,421,812 | 6/1947 | Smith et al. | 260/346.2 R |
| 2,535,058 | 12/1950 | Gleim et al. | 260/45.8 |
| 2,636,885 | 4/1953 | Wynn et al. | 260/346.2 R |
| 2,682,473 | 6/1954 | Thompson et al. | 260/346.2 M |
| 2,890,225 | 6/1959 | Gregory | 260/800 |
| 2,984,648 | 5/1961 | Williams et al. | 260/45.95 |
| 3,344,109 | 9/1967 | Ley et al. | 260/45.8 |
| 3,351,678 | 11/1967 | McBurney | 260/897 |
| 3,356,644 | 12/1967 | Lee | 260/45.95 |
| 3,824,226 | 7/1974 | Gunther et al. | 260/94.3 |
| 3,900,456 | 8/1975 | Naylor | 260/94.3 |
| 3,940,364 | 2/1976 | Layer | 260/45.8 A |

OTHER PUBLICATIONS

Coxworth, Canadian Journal of Chemistry, vol. 45, 1967, pp. 1777–1784.

Primary Examiner—Melvyn I. Marquis
Assistant Examiner—R. A. White
Attorney, Agent, or Firm—Charles A. Crehore

[57] ABSTRACT

Benzofuranylphenols are produced by (1) reacting glyoxal with a phenol in the presence of an acidic catalyst to form an acetal, and (2) thereafter partially hydrolyzing the acetal with an acidic or basic catalyst. Some benzofuranylphenols are effective stabilizers of organic materials against the deleterious effects of oxygen, heat and light. The stability of dienic polymers and styrene-acrylonitrile copolymers is particularly enhanced by incorporating stabilizing amounts of some benzofuranylphenols.

21 Claims, No Drawings

BENZOFURANYLPHENOL STABILIZERS

BACKGROUND OF THE INVENTION

Several benzofuranylphenols are described in the prior art without discussion of utility. For example, Coxsworth, 45 Can. J. Chem. 1777 (1967), teaches preparation of 2-(5-methyl-3-benzofuranyl)-4-methylphenol and 2-(5-methyl-7-t-butyl-3-benzofuranyl)-4-methyl-6-t-butylphenol. Coxworth, 44 Can. J. Chem. 1092 (1966), teaches preparation of chlorinated 2-(3-benzofuranyl)-phenols. New stabilizers and new stabilized organic compositions are desired.

SUMMARY OF THE INVENTION

Some benzofuranylphenols are effective stabilizers of a wide variety of organic materials against the deleterious effects of oxygen, heat and visible or ultraviolet light. The benzofuranylphenols are especially useful as nonstaining stabilizers for dienic polymers and styrene-acrylonitrile copolymers. Benzofuranylphenols suitable for use in this invention have the formula

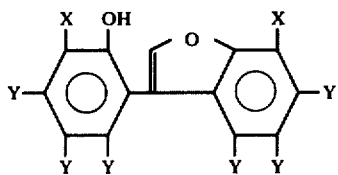

wherein each X and Y may be hydrogen, halogen, hydroxyl, or an alkyl, alkoxyl or alkylthio group containing from 1 to 8 carbon atoms, but if any X is an alkyl, alkoxyl or alkylthio group, then at least one Y must also be an alkyl, alkoxyl or alkylthio group. Also suitable are the products of a process comprising (1) reacting glyoxal with a dihydroxylated compound in the presence of an acidic catalyst, the dihydroxylated compound having the formula

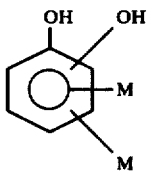

wherein each M is hydrogen, halogen or an alkyl group containing 1 to 8 carbon atoms, and (2) thereafter hydrolyzing the step (1) reaction product with an acidic or basic catalyst.

DETAILED DESCRIPTION

Benzofuranylphenols suitable for use as stabilizers have the formula below and are numbered as shown:

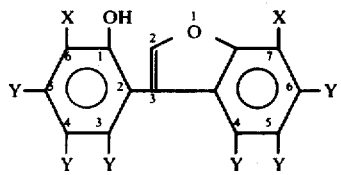

wherein each X and Y may be hydrogen, halogen, hydroxyl, or an alkyl, alkoxyl or alkylthio group containing from 1 to 8 carbon atoms, but if any X is an alkyl, alkoxyl or alkylthio group, then at least one Y must also be an alkyl, alkoxyl or alkylthio group. More preferably each X and Y may be hydrogen, bromo, chloro, hydroxyl or an alkyl or alkylthio group containing from 1 to 8 carbon atoms, but if any X is an alkyl or alkylthio group, then at least one Y must also be an alkyl or alkylthio group. Even more preferably each X and Y may be hydrogen, hydroxyl or an alkyl or alkylthio group containing from 1 to 4 carbon atoms, but if any X is an alkyl or alkylthio group, then at least one Y must also be an alkyl or alkylthio group. Examples of suitable benzofuranylphenols include 2-(6-methyl-3-benzofuranyl)-5-methylphenol, 2-(5-methyl-3-benzofuranyl)-4-methyl-phenol, 2-(5-t-butyl-3-benzofuranyl)-4-t-butylphenol, 2-(5-methyl-7-t-butyl-3-benzofuranyl)-4-methyl-6-t-butylphenol, 2-(5-t-butyl-7-methyl-3-benzofuranyl)-4-t-butyl-6-methylphenol, 2-(5,7-dimethyl-3-benzofuranyl)-4,6-dimethylphenol, 2-(4,7-dimethyl-3-benzofuranyl)-3,6-dimethylphenol, 4,73,62-(5,6-dimethyl-3-benzofuranyl)-4,5-dimethylphenol, 2-(4,6-dimethyl-3-benzofuranyl)-3,5-dimethylphenol, 2-(5,7-methylthio6-methyl3-benzofuranyl)-4,6-di-t-butylphenol, 2-(5-methylthio-6-methyl-3-benzofuranyl)-4-methylthio-5-methylphenol and the like. The reaction products of hydroquinone or 4-t-butyl catechol with glyoxal by the process described herein, are also suitable. Excellent results were obtained using 2-(5-methyl-3-benzofuranyl)-4-methylphenol, 2-(5-t-butyl-3-benzofuranyl)-4-t-butylphenol, 2-(5,7-dimethyl-3-benzofuranyl)-4,6-dimethylphenol, 2-(5,6-dimethyl-3-benzofuranyl)-4,5-dimethylphenol, 2-(4,6-dimethyl-3-benzofuranyl)-3,5-dimethylphenol, 2-(5,7-di-t-butyl-3-benzofuranyl)-4,6-di-t-butylphenol, 2-(5-methyl-7-t-butyl-3-benzofuranyl)-4 methyl-6-t-butylphenol, and 2-(5-methylthio-6-methyl-3-benzofuranyl)-4-methylthio-5-methylphenol. Excellent results were also obtained using the reaction products of hydroquinone or 4-t-butyl catechol with glyoxal described herein. In contrast, 2-(7-methyl-3-benzofuranyl)-6-methylphenol is not covered by the above formula and was found to be an ineffective antioxidant. Suitable benzofuranylphenols may be used in an amount from about 0.1 to about 10 parts by weight, more preferably from about 0.5 part to about 5 parts by weight, per 100 parts by weight of organic material to be stabilized.

Benzofuranylphenols are produced by first reacting glyoxal with a phenol in the presence of an acidic catalyst at a temperature from about 0° C to about 100° C, more preferably from about 0° C to about 50° C. An acetal is formed during the first step of the reaction, with acetal yield decreasing substantially if reaction temperature is above 50° C during the first step. After acetal formation is completed the second reaction step is performed. Water may be added to the reaction mixture, and the mixture is refluxed in order to hydrolyze the acetal and form a benzofuranylphenol. Alternatively, a solid acetal may be separated from the reaction mixture by filtration in some cases and the acetal thereafter hydrolyzed by refluxing in the presence of an acid or base catalyst.

Phenols used in the above process preferably have one unsubstituted position ortho to a hydroxyl group, but certain groups such as t-butyl and the like may occupy an ortho position and are displaced during acetal formation if the other ortho position is occupied by another substituent. Suitable phenols for use in the above process include m-cresol, p-cresol, 4-ethylphenol, 4-n-propylphenol, 4-t-butylphenol, 2-methyl-4-t-butylphenol, 2-t-butyl-p-cresol, 2,4-dimethylphenol, 2,5-dimethylphenol, 3,4-dimethylphenol, 3,5-dimethylphenol, 2,4-di-t-butylphenol, 2,4-di-t-pentylphenol, 2,6-di-t-butyl-4-methylphenol, 4-(methylthio)-m-cresol, 4-chloro-3-methylphenol and the like. Excellent results were obtained using p-cresol, 4-t-butylphenol, 2,4-dimethylphenol, 3,4-dimethylphenol, 3,5-dimethylphenol, 2-t-butyl-p-cresol, and 4-(methylthio)-m-cresol. In contrast, o-cresol was used to produce 2-(7-methyl-3-benzofuranyl)-6-methylphenol, which was an unsatisfactory stabilizer and not within the scope of the formula given heretofore. Furthermore, Bisphenol A was reacted with glyoxal by the process of this invention to form a product which was an unsatisfactory stabilizer and not within the scope of the formula given heretofore.

Also suitable as phenolic starting materials for the process described herein are dihydroxylated compounds having the formula

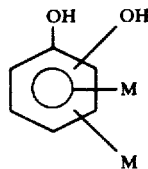

wherein each M may be hydrogen, halogen or an alkyl group containing 1 to 8 carbon atoms. More preferably each M may be hydrogen or an alkyl group containing 1 to 4 carbon atoms. The process comprises (1) reacting glyoxal with a dihydroxylated compound in the presence of an acidic catalyst and (2) thereafter hydrolyzing the step (1) reaction product with an acidic or basic catalyst. Products of the process just described may be the benzofuranylphenols described heretofore. However, complex polymeric benzofuranylphenols tend to form because of the presence of several reactive hydroxyl groups in each dihydroxylated compound molecule. Examples of suitable dihydroxylated compounds include hydroquinone, catechol, resorcinol, 4-t-butyl catechol and the like. Excellent results were obtained using hydroquinone and 4-t-butyl catechol.

The glyoxal may be used in the anhydrous form but the commercial aqueous solutions of glyoxal are more preferably used. Derivatives of glyoxal which can generate glyoxal in situ may also be used, such as glyoxal.-NaHSO$_4$. The glyoxal may be used in a molar ratio to the phenol from about 1/10 to about 10/1. More preferably, the ratio is about ½.

Acids which may be used to catalyze the reaction of glyoxal with phenols to form acetals include organic acids containing 1 to 12 carbon atoms such as acetic acid, propionic acid, benzoic acid, monoesters and diesters of orthophosphoric acid, alkaryl sulfonic acids such as p-toluenesulfonic acid, and the like; inorganic acids capable of releasing protons such as boric acid, hydrochloric acid, phosphoric acid, sulfuric acid and the like; acid activated clays capable of releasing protons such as Retrol (produced by Filtrol Corp.), bentonite and the like; acidic resins capable of releating protons such as Dowex 50-X10 (a cationic exchange resins which is a sulfonated copolymer of styrene and divinylbenzene and is produced by Dow Chemical Company) and the like; and Lewis acids capable of accepting electrons such as aluminum chloride, zinc chloride, boron trifluoride and the like. The amount of acid catalyst used may be as little as about 0.01% based on total reactant weight, or the catalyst may be used as the solvent in which the reaction is run. Mixtures of acids may also be used. Excellent results were obtained using mixtures of acetic acid and sulfuric acid, zinc chloride and hydrochloric acid, and p-toluenesulfonic acid and acetic acid.

The acids described above may also be used at higher temperature to catalyze hydrolysis of the acetal in the second reaction step, thereby forming benzofuranylphenols. Bases may be used in place of acids in the second reaction step. Suitable bases include inorganic bases such as sodium hydroxide, potassium hydroxide and the like. Excellent results were obtained using potassium hydroxide.

Acetic acid is a preferred solvent for these reactions because of its availability, boiling point, water miscibility, ability to dissolve a wide variety of phenols, and catalytic effect on the reaction. The reaction may also be run in other solvents which include carboxylic acids such as o-toluic acid, esters such as n-butyl acetate, ethers such as bis[2-(2-methoxyethoxy)ethyl]ether, alcohols such as 1-pentanol, ketones such as benzophenone, and the like. The reaction may also be run in a two-phase system where one reactant is soluble in one phase and the other reactant is soluble in a second phase, such as a hydrocarbon and water system. An emulsifying agent may be used to facilitate the reaction in the two-phase system.

A preferred method for producing benzofuranylphenols comprises mixing glyoxal and a phenol with a major amount of acetic acid and a minor amount of sulfuric acid. The reaction mixture is stirred and cooled below 30° C for about one to three hours. After that time, the temperature is raised to about 50° C, and the reaction is continued for about 0.5 to three more hours in order to complete acetal formation. The second reaction step is performed by adding water to the acetal reaction mixture and heating it to reflux temperature. After about one to five hours the acetal is acid-hydrolyzed substantially to a benzofuranylphenol.

Another preferred method for performing the second reaction step (hydrolysis) comprises separating a solid acetal from the reaction mixture by filtration, mixing the acetal with water and an acid or base, and acid-hydrolyzing or base-hydrolyzing the acetal to a benzofuranylphenol. Refluxing is generally required for acidic hydrolysis, but basic hydrolysis can be performed by simply warming the mixture to be hydrolyzed at about 50° – 100° C in a dimethyl sulfoxide solution.

The benzofuranylphenol product may be separated from the hydrolysis mixture by any of several methods. If the product is a solid it can be filtered and optionally washed with a solvent such as hexane or water. If the product is an oil it can be extracted with an aromatic solvent such as benzene. If acidic hydrolysis is used, the extract can be washed with a weak base or a basic salt solution such as Na$_2$CO$_3$ in water. If basic hydrolysis is used, the extract can be washed with a weak acid or an acidic salt solution in water such as (NH$_4$)$_2$SO$_4$ in water. The extract can then be distilled to obtain a substantially pure benzofuranylphenol.

Benzofuranylphenols within the scope of the formula recited heretofore are effective stabilizers of a wide variety of organic materials against the deleterious effects of oxygen, heat and visible or ultraviolet light. The benzofuranylphenols are nonstaining stabilizers of both natural and synthetic polymers, such as uncured and vulcanized dienic polymers. The dienic polymers are sulfur-vulcanizable and may contain about 0.5% to about 50% by weight of olefinic (>C=C<) unsaturation based upon total polymer weight. The olefinic groups may be in the polymeric main chain (backbone) or in pendant (side-chain) groups, or both. Examples of suitable dienic polymers include polymers such as natural rubber, cis-polyisoprene, cis-polybutadiene (CB), acrylonitrile-butadiene-styrene copolymers (ABS), butadiene-acrylonitrile rubbers (NBR), isoprene-acrylonitrile rubbers, polyisobutylene, polychloroprene, butadiene-styrene rubbers (SBR), isoprene-styrene rubbers and the like. Also suitable are polymers such as isoprene-isobutylene (butyl) rubbers, copolymers of conjugated dienes with lower alkyl and alkoxy acrylates such as ethyl acrylate, butyl acrylate, methoxyethyl acrylate and the like, and ethylene-propylene-diene polymers (EPDM) containing from about 0.5 percent to about 20 percent by weight of at least one dienic termonomer. Suitable EPDM dienic termonomers include conjugated dienes such as butadiene, 1,3-pentadiene, and the like; nonconjugated dienes such as 1,4-pentadiene, 1,4-hexadiene, and the like; cyclic dienes such as cyclopentadiene, dicyclopentadiene, and the like; and alkenyl norbornenes such as 5-ethylidene-2-norbornene and the like.

The dienic polymers may be vulcanized by methods known to the art. Suitable vulcanizing agents include elemental sulfur and compounds capable of yielding elemental sulfur such as tetramethylthiuram disulfide, tetraethylthiuram disulfide, dipentamethylenethiuram hexasulfide, and the like.

A broad range of compounding ingredients can be used in the dienic polymer vulcanizates, including sulfur-containing and nitrogen-containing accelerators. Examples of suitable accelerators include metal salts of dialkyl, diaryl and alkaryl dithiocarbamates, such as bismuth, copper, lead and zinc dimethyl dithiocarbamates, cadmium, selenium, tellurium and zinc diethyl dithiocarbamates, sodium and zinc dibutyl dithiocarbamates, zinc ethyl phenyl dithiocarbamate, zinc dibenzyl dithiocarbamate, and the like; other dithiocarbamates such as piperidinium pentamethylene dithiocarbamate, N-cyclohexylethyl ammonium cyclohexylethyl dithiocarbamate, N-pentamethylene-ammonium-N-pentamethylene dithiocarbamate, and the like; benzothiazoles such as 2-mercaptobenzothiazole and the zinc salt thereof, 2,2'-benzothiazyl disulfide, 2-morpholinothiobenzothiazole, 2-(2,6-dimethyl-4-morpholinothio)-benzothiazole and the like; benzothiazole-sulfenamides such as N-diethyl-2-benzothiazyl sulfenamide, N-t-butyl-2-benzothiazole sulfenamide, N-cyclohexyl-2-benzothiazole sulfenamide, N-oxydiethylene-2-benzothiazole sulfenamide and the like; thiuram sulfides such as tetramethyl thiuram disulfide, tetraethyl thiuram disulfide, dimethyl diphenyl thiuram disulfide, dipentamethylene thiuram hexasulfide and the like; thioureas such as ethylene thiourea, trimethyl thiourea, N,N'-diethyl thiourea, N,N'-dibutyl thiourea, N,N'-diphenyl thiourea, and the like; morpholines such as 4,4'-dithiomorpholine and the like; polyamines such as triethylene diamine, hexamethylene tetraamine, tricretonylidene tetraamine, and the like; aldehyde-amine condensation products such as acetaldehyde-ammonia, heptaldehyde-ammonia, butyraldehyde-aniline, and the like, imidazolines such as 2-mercaptoimidazoline, and the like; and guanidines such as diphenyl guanidine, di-o-tolyl guanidine, and the like. Excellent results were obtained using 2-morpholinothiobenzothiazole.

Benzofuranylphenols within the scope of the formula recited heretofore are also effective nonstaining antioxidants in styrene-acrylonitrile copolymers. Suitable copolymers for use in the compositions of this invention contain polymerized therein (1) from about 50% to about 90% by weight based upon total copolymer weight of styrene, or at least one alkyl styrene, alkoxy styrene or halostyrene, or a mixture thereof, wherein the alkyl or alkoxy group contains from 1 to 8 carbon atoms, (2) from about 10% to about 50% by weight based upon total copolymer weight of at least one vinyl nitrile having the formula

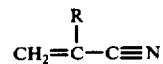

wherein R is hydrogen or an alkyl radical containing from 1 to 3 carbon atoms, and (3) from 0% to about 20% by weight based upon total copolymer weight of at least one other monoolefin. Preferred alkyl styrenes are those wherein an alkyl group contains from 1 to 6 carbon atoms, more preferably from 1 to 4 carbon atoms. Preferred alkoxy styrenes are those wherein an alkoxy group contains from 1 to 6 carbon atoms, more preferably from 1 to 4 carbon atoms. Preferred halostyrenes are those wherein a halogen group is chloro or bromo. Examples of suitable alkyl styrenes, alkoxy styrenes and halostyrenes include methyl styrene, ethyl styrene, methoxyethylstyrene, chlorostyrene, dichlorostyrene, and the like. Examples of suitable vinyl nitriles include acrylonitrile, methacrylonitrile, ethacrylonitrile, and the like. Excellent results were obtained using copolymers of styrene and acrylonitrile.

Other compounding ingredients usable in the dienic polymer compositions and styrene-acrylonitrile copolymers include fillers such as carbon blacks, calcium and magnesium carbonates, calcium and barium sulfates, aluminum silicates, silicon dioxide, phenol-formaldehyde and polystyrene resins, asbestos, and the like; plasticizers and extenders including dialkyl and diaryl acid esters such as diisobutyl, diisooctyl, diisodecyl and dibenzyl oleates, stearates, sebacates, azelates, phthalates, and the like, and naphthenic and paraffinic oils, castor oil, tall oil and the like; and antioxidants, antiozonants and stabilizers such as di-β-naphthyl-p-phenylenediamine, phenyl-β-naphthylamine, N,N'-di-(2-octyl)-p-phenylenediamine, 2,2'-methylene-bis (4-methyl-6-t-butylphenol), 2,6-di-t-butyl-p-cresol, 2,2'-thiobis(4-methyl-6-t-butylphenol), distearyl thiodipropionate, dilauryl thiodipropionate, 2,4-bis(4-hydroxy-3,5-t-butylphenoxy)-6-(n-octylthio)-1,3,5-triazine, tetrakis methylene 3-(3',5'-di-t-butyl-4'-hydroxyphenyl)propionate methane, 4-isopropylamino diphenylamine, tri(nonylated phenyl)phosphite, and the like, Other compounding ingredients may also be used, such as pigments, tackifiers, flame retardants, fungicides, and the like.

In addition to polymeric materials, the present benzofuranylphenols act to stabilize a wide variety of other organic materials. Such materials include: waxes; synthetic and petroleum-derived lubricating oils and greases; animal oils such as fat, tallow, lard, cod-liver oil, sperm oil and the like; vegetable oils such as castor, linseed, peanut, palm, cotton seed and the like; fuel oil; diesel oil; gasoline; and the like.

The following examples illustrate the present invention more fully.

EXAMPLE 1

Preparation of
2-(7-methyl-3-benzofuranyl)-6-methylphenol o-cresol (44 g. or 0.4 mole), 40% aqueous glyoxal (30 g. or 0.2 mole), and acetic acid (200 ml.) were mixed together. Concentrated sulfuric acid (80 ml. or 1.5 mole) was added to the reaction mixture with stirring over a 60-minute period. The mixture was stirred for a total of about 3 hours with cooling as needed to keep reaction temperature at about 30° C. The mixture was heated thereafter to 50° C and stirred for about 1 hour. Water (100 ml.) was added and the mixture refluxed for about 1.5 hours. The mixture then was cooled and poured into 2 liters of water, and a solid was separated therefrom. The solid was filtered and washed first with water and then with 0.1 normal $Na_2CO_3$ solution in water. The product weighed 44 g. The 2-(7-methyl-3-benzofuranyl)-6-methylphenol was found to be an unsatisfactory stabilizer in a vulcanized rubber composition.

EXAMPLE 2

Preparation of
2-(5-methyl-3-benzofuranyl)-4-methylphenol p-cresol (86.4 g. or 0.8 mole), 40% aqueous glyoxal (80 g. or 1.4 mole), and acetic acid (200 ml.) were mixed together. Concentrated sulfuric acid (80 ml.) was added to the reaction mixture with stirring over a 60-minute period. The mixture was stirred for a total of about 3 hours with cooling as necessary to keep reaction temperature at about 30° C. The mixture was then allowed to stand overnight. The acetal intermediate formed and was a solid. It was collected by filtration, washed with 400 of water, and allowed to dry. It weighed 90 g. (95% yield based on p-cresol) and melted at 150°–165° C. This solid was dissolved in 200 ml. of acetic acid, 10 ml. of water, and 2 ml. of concentrated sulfuric acid. This solution was refluxed for 2 hours, cooled and neutralized with a solution of 4 g. of sodium hydroxide in 10 ml. of water. The solvents were distilled to give 77 g. of a black viscous oil. This oil was distilled to give a light yellow oil (b.p. 120°–145° C/0.5 mm).

EXAMPLE 3

Preparation of
2-(5-t-butyl-3-benzofuranyl)-4-t-butylphenol 4-t-Butylphenol (60 g. or 0.4 mole), 40% aqueous glyoxal (30 g. or 0.2 mole), and 200 ml. of acetic acid were mixed together. Concentrated sulfuric acid (80 ml.) was slowly added (1 hour at 30° C), and the mixture was stirred for another 2 hours at 30° C and thereafter heated to 50° C for 0.5 hour. 100 ml. of water was added and the mixture was refluxed for 1.5 hours, cooled, poured into 1.5 liters of water, and the product separated. The oily product was washed with 0.1N $Na_2CO_3$ solution.

EXAMPLE 4

Preparation of
2-(5-t-butyl-7-methyl-3-benzofuranyl)-4-t-butyl-6-methylphenol

2-Methyl-4-t-butylphenol (64 g. or 0.4 mole) and acetic acid (200 ml.) were mixed together. Concentrated sulfuric acid (80 ml.) was added to the reaction mixture with stirring over a 60-minute period. The mixture was stirred for a total of about 2 hours with cooling as needed to keep reaction temperature at about 30° C. The mixture was heated thereafter to 50° C and stirred for about 0.5 hour. Water (100 ml.) was added and the mixture refluxed for about 1.5 hours. The mixture then was cooled and pured into 1.5 liters of water, and a black oil was separated therefrom. The oil was washed with a 0.1 normal $Na_2CO_3$ solution in water, and unreacted 2-methyl-4-t-butylphenol was removed by distillation. The product weighed 76 g. The product's IR spectrum was consistent with the assigned structure of 2-(5-t-butyl-7-methyl-3-benzofuranyl)-4-t-butyl-6-methylphenol.

EXAMPLE 5

Preparation of
2-(5,7-dimethyl-3-benzofuranyl)-4,6-dimethylphenol 2,4-Dimethylphenol (49 g. or 0.4 mole), 40% aqueous glyoxal (29 g. or 0.2 mole), and acetic acid (250 ml.) were stirred together and 80 ml. of concentrated sulfuric acid added in 1 hour. The reaction temperature was maintained between 20° – 30° C by cooling during the addition. The temperature was raised to 50° C for 1 hour. The mixture was cooled, filtered, and washed with water to separate an acetal intermediate, which was refluxed for 4 hours with 250 ml. of acetic acid and 5 ml. of concentrated hydrochloric acid. The cool reaction mixture was poured into 1.5 liters of water and the oil separated. It weighed 32 g., and its IR spectrum was consistent with the assigned structure of 2-(5,7-dimethyl-3-benzofuranyl)-4,6-dimethylphenol.

EXAMPLE 6

Preparation of
2-(5-methyl-7-t-butyl-3-benzofuranyl)-4-methyl-6-t-butylphenol

A mixture of zinc chloride (3 g.), 2-t-butyl-p-cresol (65.7 g. or 0.5 mole), and 30% aqueous glyoxal (20 g. or 0.5 mole), and 30% aqueous glyoxal (20 g. or 0.1 mole) was stirred and gaseous HCl bubbled into the mixture for 0.5 hour. The temperature was kept below 35° C by cooling. The mixture stood overnight, after which HCl was bubbled through the mixture for 3 hours more with the temperature maintained between 10° – 20° C by cooling. A light gray solid formed. This solid was filtered and washed first with water and then 0.1N $Na_2CO_3$ solution. The white solid melted at 188° – 192° C and was the acetal described in U.S. Pat. No. 2,515,909. The acetal, weighing 11 g., was slurried in 100 ml. of dimethylsulfoxide. A solution of potassium hydroxide (10 g.), ethanol (100 ml.), and dimethylsulfoxide (100 ml.) was added directly to the acetal slurry. This mixture was heated to reflux under nitrogen for 4 hours. The mixture was poured into 1 liter of water which contained 15 ml. of concentrated hydrochloric acid. A solid formed and was collected by filtration and washed with water. It weighed 9 g. and melted at 132° – 134° C. Its paramagnetic resonance and IR spectra were consistent with the assigned structure of 2-(5-methyl-7-t-butyl-3-benzofuranyl)-4-methyl-6-t-butylphenol.

EXAMPLE 7

Preparation of
2-(5,6-dimethyl-3-benzofuranyl)-4,5-dimethylphenol

To a mixture of 3,4-dimethylphenol (62 g. or 0.5 mole), 40% aqueous glyoxal (23 g. or 0.15 mole), and acetic acid (200 ml.), was slowly added (0.5 hour) 30 ml. of concentrated sulfuric acid. The mixture was stirred at 50° C for 2 hours, cooled, and poured into 1.5 liters of water to give 44 g. of a solid acetal. 40 g. of this acetal was slurried in 250 ml. of dimethylsulfoxide, and a solution of 40 g. of potassium hydroxide in 250 ml. of methanol and 250 ml. of dimethylsulfoxide was added. This mixture was refluxed for 2 hours, cooled, poured into 2 liters of water, and extracted with benzene. The benzene was removed by distillation to give 44 g. of a dark oil. Its IR spectrum was consistent with the assigned structure of 2-(5,6-dimethyl-3-benzofuranyl)-4,5-dimethylphenol.

EXAMPLE 8

Preparation of
2-(4,6-dimethyl-3-benzofuranyl)-3,5-dimethylphenol

A stirred mixture of 3,5-dimethylphenol (25 g. or 0.2 mole), 40% aqueous glyoxal (15 g. or 0.1 mole) and acetic acid (150 ml.) was maintained at 30° C while 15 ml. of concentrated sulfuric acid was added in 0.5 hour. The mixture was stirred 2 hours more at room temperature and then at 50° C for 0.5 hour. Water (35 ml.) was added and the mixture refluxed for 1.5 hours. It was cooled and poured into 1 liter of water to give 18 g. of a black solid. The solid was separated by filtration and had an IR spectrum consistent with its structural assignment of 2-(4,6-dimethyl)- 3-benzofuranyl-3,5-dimethylphenol.

EXAMPLE 9

Preparation of
2-(5,7-di-t-butyl-3-benzofuranyl)-4,6-di-t-butylphenol

A mixture of 2,4-di-t-butylphenol (82 g. or 0.4 mole), 40% aqueous glyoxal (30 g. or 0.2 mole), and acetic acid (400 ml.) was treated with 80 ml. of concentrated sulfuric acid while maintaining the temperature at 30° C. After 2 hours, the solid was collected by filtration. Vapor phase chromatography showed that it was 30% starting phenol and 70% acetal. The phenol was removed by washing with methanol. The substantially pure acetal remained, melted at 236°–238° C, and weighed 51 g. This acetal (30 g.) was dissolved in 100 ml. of benzene and 200 ml of dimethylsulfoxide. The acetal solution was treated with a solution of 20 g. of potassium hydroxide in 200 ml. of methanol and 200 ml. of dimethylsulfoxide. This mixture was refluxed for 2 hours, cooled, poured into 1 liter of water, acidified with concentrated hydrochloric acid and extracted with ether. The ether extract was washed with water and distilled to give 34 g. of a yellow oil (b.p. 200° C/ 1 mm). Its VPC and IR spectra were consistent with the assigned structure of 2-(5,7-di-t-butyl-3-benzofuranyl)-4,6-di-t-butylphenol.

EXAMPLE 10

Preparation of
2-(5-methylthio-6-methyl-3-benzofuranyl)-4-methylthio-5-methylphenol A mixture of 4-(methylthio)-m-cresol (31 g. or 0.2 mole), 40% aqueous glyoxal (15 g. or 0.1 mole), and 150 ml. of acetic acid was treated with 15 ml. of concentrated sulfuric acid while maintaining the temperature below 30° C for 2 hours. Temperature was raised thereafter to 50° C for 0.5 hour, 30 ml. of water was added to the mixture, and it was refluxed for 1.5 hours, cooled, and poured into 1 liter of water. An oil was separated and washed with a 0.1N $Na_2CO_3$ solution to yield 2-(5-methylthio-6-methyl-3-benzofuranyl)-4-methylthio-5-methylphenol.

EXAMPLE 11

Reaction of hydroquinone and glyoxal, followed by hydrolysis

A mixture of hydroquinone (66 g. or 0.6 mole), 40% aqueous glyoxal (90 g. or 0.6 mole), and 500 ml. of acetic acid was treated with 60 ml. of concentrated sulfuric acid while maintaining the temperature at 30° C for 2 hours. The mixture was then heated for 2 hours at 40° – 50° C., poured into 2 liters of water, filtered, washed with 0.1N $Na_2CO_3$, and dried to yield 62 g. of a gray solid acetal. This acetal (25 g.) was stirred with 100 ml. of dimethylsulfoxide. To this mixture was added a solution of 25 g. of potassium hydroxide, 200 ml. of methanol, and 200 ml. of dimethylsulfoxide. A dark brown mixture resulted and was stirred and refluxed for 4 hours. It was poured into 2 liters of water and acidified with concentrated hydrochloric acid. A black resin was collected by filtration and washed with 0.1N $Na_2CO_3$. The resin's IR spectrum was consistent with a polymeric benzofuranylphenol structure.

EXAMPLE 12

Reaction of 4-t-butyl catechol and glyoxal, followed by hydrolysis

A mixture of 4-t-butyl catechol (32.3 g. or 0.2 mole) 40% aqueous glyoxal (15 g. or 0.1 mole) and acetic acid (150 ml.) was treated with 15 g. of concentrated sulfuric acid while maintaining the temperature at 30° C for 2 hours. The mixture was then heated for 0.5 hour at 50° C, poured into 35 ml. water and stirred and refluxed for 1.5 hours. The mixture was cooled and poured into 1 liter of water. A black oil formed and was extracted with benzene and washed with a 0.1N $Na_2CO_3$ solution. The extract was distilled to give 21 g. of product.

EXAMPLES 13 – 31

Examples 13 – 31 demonstrate stabilizing properties of benzofuranylphenols in cured rubber vulcanizates. A master batch was prepared by mixing the following materials in a banbury mixer:

TABLE I

| Materials | Parts by Weight |
| --- | --- |
| Ribbed Smoked Sheet Natural Rubber | 100.0 |
| HAF Carbon Black | 50.0 |
| Zinc Oxide | 5.0 |
| Stearic Acid | 3.0 |
| Sulfur | 2.5 |
| | 160.5 |

In each example, 176 g. of the masterbatch described in Table I was compounded and cured with 1.1 gram of 2-morpholinothiobenzothiazole accelerator and 1.1 gram of a given stabilizer. The compounding and curing procedure was as follows. A 4-inch, 2-roll mill was heated to 160° F and each ingredient was charged to the mill in the order listed, with thorough milling between each addition. Each milled rubber composition was sheeted off the mill and cut into approximate 6 in. × 6 in. × 0.090 in. sections. The sections were wrapped separately in aluminum foil and cured for 35 minutes at 302° F.

Physical testing of the vulcanizates was performed, and the results are set forth in Tables II, III, and IV. 300% modulus, tensile strength and ultimate elongation were determined according to ASTM D412-68 using Die C dumbbells. Test tube aging was performed according to ASTM D865-62 for 24 hours at 100° C. Crack Growth Test results in Table II were measured using the B. F. Goodrich Rotating Ring Crack Growth Test described in 38 *Rubber Chemistry & Technology* 714 (1965). Standard conditions used for the latter test were 70° C., 3 lbs. load and 300 cycles/minute.

The data in Tables II, III and IV indicates that the benzofuranylphenols tested have stabilizing properties as good as or better than control stabilizers when tested in cured rubber vulcanizates.

TABLE II

AGING CHARACTERISTICS OF BENZOFURANYLPHENOLS IN NATURAL RUBBER VULCANIZATES

| | | | Test Tube Aging (24 hrs. at 100° C) | | | | | | Crack Growth Test | |
|---|---|---|---|---|---|---|---|---|---|---|
| | | | 200% Modulus Day(s) | | Tensile Strength(psi) Day(s) | | Elongation % Day(s) | | | |
| Ex.* | Stabilizer | Starting Phenol | 0 | 1 | 0 | 1 | 0 | 1 | Hrs. to Failure | Crack Length In Units** |
| 13* | None | — | — | 1380 | 3250 | 1600 | 360 | 220 | 12 | 12.6 |
| 14* | 2,2'-Methylenebis-(4-methyl-6-t-butylphenol) | — | — | 1450 | 3600 | 2400 | 400 | 270 | 24 | 13.9 |
| 15* | Mixture of about 40% 2-t-butyl-4,4'-isopropylidenediphenol and about 60% 2,2'-di-t-butyl-4,4'-isopropylidenediphenol | — | — | 1500 | 3500 | 2000 | 380 | 250 | 24 | 14.0 |
| 16* | Mixture of styrenated phenols | — | — | 1600 | 3700 | 2650 | 390 | 290 | 24 | 13.8 |
| 17* | P,p'-di-(1,1,3,3-tetramethylbutyl)diphenylamine | — | — | 1700 | 3550 | 3150 | 390 | 320 | 28 | 13.9 |
| 18 | 2-(5,6-Dimethyl-3-benzofuranyl)-4,5-dimethylphenol | 3,4-Dimethylphenol | — | 1400 | 3700 | 2600 | 430 | 300 | 28 | 14.1 |

*Control
**1 Unit = 0.025 inch

TABLE III

AGING CHARACTERISTICS OF BENZOFURANYLPHENOLS IN NATURAL RUBBER VULCANIZATES

| | | | 300% Modulus Day(s) | | | | Tensile Strength (psi) Day(s) | | | | Ultimate Elongation (%) 261 Day(s) | | | |
|---|---|---|---|---|---|---|---|---|---|---|---|---|---|---|
| Ex. | Stabilizer | Starting Phenol | 0 | 1 | 2 | 3 | 0 | 1 | 2 | 3 | 0 | 1 | 2 | 3 |
| 19* | None | — | 1900 | — | — | — | 2900 | 1600 | 900 | 900 | 390 | 270 | 200 | 190 |
| 20* | 2,2'-Methylenebis(4-methyl-6-t-butylphenol) | — | 2600 | 300 | — | — | 3900 | 3150 | 2200 | 2200 | 420 | 310 | 220 | 220 |
| 21* | Stabilizer** | — | 2000 | 2300 | 2450 | 2300 | 3200 | 2950 | 2450 | 2300 | 430 | 360 | 290 | 280 |
| 22 | 2-(5-Methyl-3-benzofuranyl)-4-methylphenol | P-cresol | 2600 | — | — | — | 3900 | 2800 | 2000 | 1900 | 420 | 290 | 220 | 210 |
| 23 | 2-(5-t-Butyl-3-benzofuranyl)-4-t-butylphenol | 4-t-Butylphenol | 2450 | — | — | — | 3800 | 2200 | 1600 | 1300 | 420 | 260 | 210 | 190 |
| 24 | Hydrolyzed reaction product of hydroquinone and glyoxal from Ex.11 | Hydroquinone | 2450 | — | — | — | 3600 | 2450 | 1400 | 1200 | 390 | 280 | 200 | 180 |

*Control
**Stabilizer having the formula:

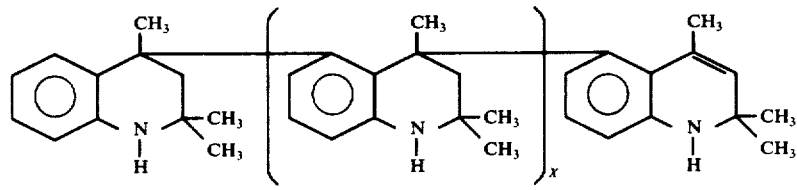

where X is 0 to 10

TABLE IV

AGING CHARACTERISTICS OF BENZOFURANYLPHENOLS IN NATURAL RUBBER VULCANIZATES

| | | 300% Modulus Day(s) | Tensile Strength (psi) Day(s) | | | | Ultimate Elongation (%) Day(s) | | | |
|---|---|---|---|---|---|---|---|---|---|---|
| | Starting | | | | | | | | | |
| Stabilizer | Phenol | 0 | 0 | 1 | 2 | 3 | 0 | 1 | 2 | 3 |
| 25* None | — | 2700 | 2800 | 1300 | 600 | 550 | 310 | 180 | 150 | 120 |

TABLE IV-continued

AGING CHARACTERISTICS OF BENZOFURANYLPHENOLS IN NATURAL RUBBER VULCANIZATES

| | | Starting Phenol | 300% Modulus Day(s) | Tensile Strength (psi) Day(s) | | | | Ultimate Elongation (%) Day(s) | | | |
|---|---|---|---|---|---|---|---|---|---|---|---|
| | Stabilizer | | 0 | 0 | 1 | 2 | 3 | 0 | 1 | 2 | 3 |
| 26* | 2,2'-Methylenebis(4-methyl-6-t-butylphenol) | — | 2650 | 3400 | 2200 | 1350 | 1000 | 370 | 250 | 170 | 140 |
| 27* | t-Butylated Bisphenol A | — | 2600 | 3400 | 2450 | 1800 | 1500 | 375 | 270 | 200 | 190 |
| 28 | 2-(5-Methyl-3-benzofuranyl)-4-methylphenol | P-cresol | 2600 | 3700 | 2050 | 1100 | 800 | 380 | 250 | 160 | 140 |
| 29 | Hydrolyzed reaction product of 4-t-butyl catechol from Ex.12 | 4-t-Butyl-catechol | 2500 | 3400 | 1500 | 950 | 700 | 380 | 200 | 160 | 140 |
| 30 | 2-(4,6-Dimethyl-3-benzofuranyl)-3,5-dimethylphenol | 3,5-Dimethyl-phenol | 2700 | 3600 | 1500 | 1050 | 850 | 390 | 200 | 160 | 140 |
| 31 | Mixture** | | 2600 | 3600 | 1900 | 1400 | 1000 | 390 | 230 | 200 | 150 |

*Control **Mixture of benzofuranylphenols produced by the process described at pp. 3-13 from a phenol mixture having this approximate composition: 2% 2,4-dimethylphenol, 18% 3,5-dimethylphenol, 30% 3,4-dimethylphenol and 50% higher alkylated phenols.

EXAMPLES 32 – 34

Examples 32 – 34 demonstrate stabilizing properties of benzofuranylphenols in uncured SN rubber. In each example, 0.68 g. of a given stabilizer was mixed with 68 g. of reprecipitated SN rubber in a Brabender Plasticorder for 2 minutes at 80° C. Each sample was prepared and tested for Mooney viscosity before and after aging according to ASTM D-1646-72 using a large rotor and a 1-minute warm-up time. Mooney buttons were aged at 70° C for 10 days in an oven according to ASTM D-573-67. Test results are summarized in Table V. The Mooney viscosity data indicates that the benzofuranylphenols maintain Mooney viscosity as well as or better than the control stabilizer.

molecular weight of about 51,000. In each example, about 75 g. of SAN copolymer was mixed in a Brabender Plasticorder fitted with a cam head. Mixing was performed at 175° C and 30 rpm until fluxing occurred (typically about 1.5 minutes after mixing began). At that time, 75 g. more of SAN copolymer and 0.75 gram of a given stabilizer were charged to the Brabender, and mixing was continued for about another 2.5 minutes. The mix was dumped, cold-pressed into sheets about 0.25 inch thick, cut into 0.25 inch cubes, pressed into 6 in. × 6 in. × 0.02 in. sheets at 175° C for about 4.5 minutes, cooled, and cut into 1 in. × 1 in. × 0.02 in. squares which were aged at 100° C in a circulating oven for varying times shown in Table VI. A Brinkman Fiber Optics Probe Colorimeter Model PC-100 was used to

TABLE V

STABILIZATION OF SN RUBBER WITH BENZOFURANYLPHENOLS

| | | | Mooney Viscosity After No Aging | | | Mooney Viscosity After Aging 10 Days at 70° C | | | |
|---|---|---|---|---|---|---|---|---|---|
| Ex. | Stabilizer | Starting Phenol | Immediate | 4 Min. Shearing Time | 10 Min. Shearing Time | Immediate | 4 Min. Shearing Time | 10 Min. Shearing Time | Average Viscosity Loss(%) |
| 32* | 2,6-Di-t-butyl-p-cresol | — | 75 | 65 | 62 | 65 | 58 | 55 | 12 |
| 33 | 2-(5,7-Dimethyl-3-benzofuranyl)-4,6-dimethylphenol | 2,4-Dimethyl-phenol | 76 | 67 | 64 | 69 | 63 | 60 | 7 |
| 34 | 2-(5-Methylthio-6-methyl-3-benzofuranyl)-4-methylthio-5-methyl-phenol | 4(Methyl-thio)-m-cresol | 78 | 69 | 67 | 66 | 62 | 60 | 12 |

*Control

EXAMPLES 35 – 42

Examples 35 – 42 demonstrate stabilizing properties of benzofuranylphenols in a styrene-acrylonitrile (SAN) copolymer composition. The SAN copolymer contained about 30% by weight acrylonitrile based upon total copolymer weight and had a weight-average molecular weight of about 118,000 and a number-average measure percent light transmission at 450 nm of heat-aged samples in comparison to unaged samples. Reduced light transmission indicates increased color development and is a measure of increased copolymer oxidation. Test results are summarized in Table VI. The data indicates the benzofuranylphenols have stabilizing properties as good as or better than the control stabilizers.

TABLE VI

STABILIZATION OF A STYRENE-ACRYLONITRILE COPOLYMER WITH BENZOFURANYLPHENOLS

| | | | % Transmission after Aging at 100° C. | | | |
|---|---|---|---|---|---|---|
| Ex. | Stabilizer | Starting Phenol | 0 Days | 10 Days | 50 Days | 100 Days |
| 35* | 4,4'-Butylidene-bis(6-t-butyl-m-cresol) | — | 100 | 88 | 60 | 42 |
| 36* | 1,1,3-Tris(2-methyl-4-hydroxy-5-t-butyl)butane | — | 100 | 93 | 74 | 50 |
| 37* | Mixture of tri(monononylphenyl)phosphite and tri(dinonylphenyl)phosphite | — | 100 | 94 | 66 | 43 |
| 38 | 2-(5-Methyl-3-benzofuranyl)-4-methylphenol | P-cresol | 100 | 91 | 75 | 66 |
| 39 | 2-(5,6-Dimethyl-3-benzofuranyl)-4,5-dimethylphenol | 3,4-Dimethyl- | 100 | 85 | 75 | 71 |

TABLE VI-continued
STABILIZATION OF A STYRENE-ACRYLONITRILE COPOLYMER WITH BENZOFURANYLPHENOLS

| Ex. | Stabilizer | Starting Phenol | % Transmission after Aging at 100° C. | | | |
|---|---|---|---|---|---|---|
| | | | 0 Days | 10 Days | 50 Days | 100 Days |
| 40 | 2-(5-Methyl-7-t-butyl-3-benzofuranyl)-4-methyl-6-t-butylphenol | phenol 2-t-Butyl-4-methylphenol | 100 | 78 | 70 | 50 |
| 41 | 2-(5-t-Butyl-7-methyl-3-benzofuranyl)-4-t-butyl-6-methylphenol | 2-methyl-4-t-butylphenol | 100 | 90 | 82 | 70 |
| 42 | 2-(5,7-Di-t-butyl-3-benzofuranyl)-4,6-di-t-butylphenol | 2,4-di-t-butylphenol | 100 | 92 | 69 | 66 |

*Control

I claim:

1. A stabilized composition comprising (A) 100 parts by weight of at least one polymer selected from the group consisting of (1) diene polymers and (2) a polymer containing polymerized therein (a) from about 50% to about 90% by weight based upon total copolymer weight of styrene, or at least one alkyl styrene, alkoxy styrene or halostyrene, or a mixture thereof, wherein the akyl or alkoxy group contains from 1 to 8 carbon atoms, (b) from about 10% to about 50% by weight based upon total copolymer weight of at least one vinyl nitrile having the formula

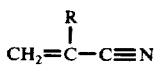

wherein R is hydrogen or an alkyl radical containing from 1 to 3 carbon atoms, and (c) from 0% to about 20% by weight of at least one monoolefin and (B) from about 0.1 part to about 10 parts by weight of at least one benzofuranylphenol having the formula

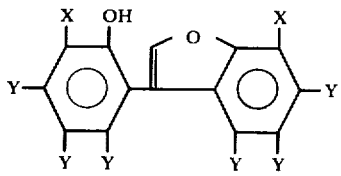

wherein each X and Y is hydrogen, or an alkyl, alkoxyl or alkylthio group containing from 1 to 8 carbon atoms, but if any X is an alkyl, alkoxyl or alkylthio group, then at least one Y must also be an alkyl, alkoxyl or alkylthio group.

2. A composition of claim 1 wherein the polymer is a dienic polymer.

3. A composition of claim 2 wherein each X and Y is hydrogen, or an alkyl or alkylthio group containing from 1 to 8 carbon atoms.

4. A composition of claim 3 wherein each X and Y is hydrogen, or an alkyl or alkylthio group containing from 1 to 4 carbon atoms.

5. A composition of claim 4 wherein the dienic polymer is an isoprene homopolymer or copolymer.

6. A composition of claim 6 wherein the dienic polymer is polyisoprene.

7. A vulcanized composition of claim 2.

8. A composition of claim 2 wherein said benzofuranylphenol is 2-(5-methyl-3-benzofuranyl)-4-methylphenol.

9. A composition of claim 2 wherein said benzofuranylphenol is 2-(5-t-butyl-3-benzofuranyl)-4-t-butylphenol.

10. A composition of claim 2 wherein said benzofuranylphenol is 2-(5,7-dimethyl-3-benzofuranyl)-4,6-dimethylphenol.

11. A composition of claim 2 wherein said benzofuranylphenol is 2-(5,6-dimethyl-3-benzofuranyl)-4,5-dimethylphenol.

12. A composition of claim 2 wherein said benzofuranylphenol is 2-(4,6-dimethyl-3-benzofuranyl)-3,5-dimethylphenol.

13. A composition of claim 2 wherein said benzofuranylphenol is 2-(5-methylthio-6-methyl-3-benzofuranyl)-4-methylthio-5-methylphenol.

14. A composition of claim 1 wherein the polymer contains copolymerized therein (1) from about 50% to about 90% by weight based upon total copolymer weight of styrene, or at least one alkyl styrene, alkoxy styrene or halostyrene, or a mixture thereof, wherein the alkyl or alkoxy group contains from 1 to 8 carbon atoms, (2) from about 10% to about 50% by weight based upon total copolymer weight of at least one vinyl nitrile having the formula

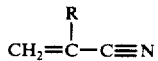

wherein R is hydrogen or an alkyl radical containing from 1 to 3 carbon atoms, and (3) from 0% to about 20% by weight of at least one monoolefin.

15. A composition of claim 14 wherein each X and Y is hydrogen, or an alkyl or alkylthio group containing from 1 to 8 carbon atoms.

16. A composition of claim 15 wherein each X and Y is hydrogen, or an alkyl or alkylthio group containing from 1 to 4 carbon atoms.

17. A composition of claim 14 wherein said benzofuranylphenol is 2-(5-methyl-3-benzofuranyl)-4-methylphenol.

18. A composition of claim 14 wherein said benzofuranylphenol is 2-(5,6-dimethyl-3-benzofuranyl)-4,5-dimethylphenol.

19. A composition of claim 14 wherein said benzofuranylphenol is 2-(5-methyl-7-t-butyl-3-benzofuranyl)-4-methyl-6-t-butylphenol.

20. A composition of claim 14 wherein said benzofuranylphenol is 2-(5-t-butyl-7-methyl-3-benzofuranyl)-4-t-butyl-6-methylphenol.

21. A composition of claim 14 wherein said benzofuranylphenol is 2-(5,7-di-t-butyl-3-benzofuranyl)-4,6-di-t-butylphenol.

* * * * *